United States Patent
Yu

(10) Patent No.: US 10,413,364 B1
(45) Date of Patent: Sep. 17, 2019

(54) INTERNAL ORGAN LOCALIZATION OF A SUBJECT FOR PROVIDING ASSISTANCE DURING SURGERY

(71) Applicant: SONY CORPORATION, Tokyo (JP)

(72) Inventor: Liangyin Yu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/058,502

(22) Filed: Aug. 8, 2018

(51) Int. Cl.
| | |
|---|---|
| *G06K 9/00* | (2006.01) |
| *A61B 34/10* | (2016.01) |
| *G06K 9/62* | (2006.01) |
| *G06T 7/90* | (2017.01) |
| *G06T 7/40* | (2017.01) |
| *G06T 19/20* | (2011.01) |
| *H04N 5/445* | (2011.01) |
| *A61B 1/313* | (2006.01) |
| *A61B 1/04* | (2006.01) |
| *A61B 5/00* | (2006.01) |
| *A61B 34/20* | (2016.01) |
| *G06T 7/73* | (2017.01) |
| *A61B 90/00* | (2016.01) |

(52) U.S. Cl.
CPC .............. *A61B 34/10* (2016.02); *A61B 1/04* (2013.01); *A61B 1/3132* (2013.01); *A61B 5/7267* (2013.01); *A61B 34/20* (2016.02); *G06K 9/6256* (2013.01); *G06T 7/40* (2013.01); *G06T 7/75* (2017.01); *G06T 7/90* (2017.01); *G06T 19/20* (2013.01); *H04N 5/445* (2013.01); *A61B 2034/107* (2016.02); *A61B 2034/2057* (2016.02); *A61B 2034/2065* (2016.02); *A61B 2090/373* (2016.02); *G06T 2207/10016* (2013.01); *G06T 2207/10068* (2013.01); *G06T 2207/20076* (2013.01); *G06T 2207/20081* (2013.01); *G06T 2207/30204* (2013.01); *G06T 2219/2016* (2013.01)

(58) Field of Classification Search
None
See application file for complete search history.

(56) References Cited

U.S. PATENT DOCUMENTS

| | | | |
|---|---|---|---|
| 8,073,528 | B2 | 12/2011 | Zhao et al. |
| 9,526,587 | B2 | 12/2016 | Zhao et al. |
| 2005/0090711 | A1 | 4/2005 | Fuchs et al. |
| 2006/0258938 | A1 | 11/2006 | Hoffman et al. |
| 2014/0058407 | A1 | 2/2014 | Tsekos et al. |

*Primary Examiner* — Atiba O Fitzpatrick
(74) *Attorney, Agent, or Firm* — Chip Law Group

(57) ABSTRACT

An apparatus and method for localization of an internal organ of a subject to provide assistance during surgery, includes capture of a sequence of video frames of one or more internal organs in a body of a subject by insertion of an image capture device in a body of the subject. The apparatus further includes circuitry that computes appearance data of an internal organ of interest in a test video frame selected from the captured sequence of video frames. Orientation data of the internal organ of interest is determined within the body of the subject based on a known orientation of the image capture device and a maximum correlation of the test video frame with a specified anatomical template for the internal organ of interest. Supplemental information is generated to localize at least a portion of the internal organ of interest of the subject in the surgery.

20 Claims, 7 Drawing Sheets

INTERNAL ORGAN LOCALIZATION OF A SUBJECT FOR PROVIDING ASSISTANCE DURING SURGERY

CROSS-REFERENCE TO RELATED APPLICATIONS/INCORPORATION BY REFERENCE

None.

FIELD

Various embodiments of the disclosure relate to organ localization and computer-assisted surgery technologies. More specifically, various embodiments of the disclosure relate to an apparatus and method for an internal organ localization of a subject for providing assistance during surgery.

BACKGROUND

Advancements in the field of medical imaging techniques and associated sensors and/or devices have made it possible to view the interior of a human or animal body for clinical analysis and medical purposes. Typically, a surgeon inserts an instrument carrying a miniaturized camera, for example, a laparoscope, within a patient's body to look at certain internal organs, such as liver, spleen, kidney, and the like, during a surgery or clinical examination. The instrument may be inserted through a small incision in the patient's body, for example, an abdominal wall of the patient's body.

In certain scenarios, the internal organ that has to be examined or resected may not be clearly visible to a surgeon because of the presence of blood, gases, and tissues that may lie in the field of view of the instrument. Further, the view of the internal organ may be blocked by tumor growth on the same organ or neighboring organs. The presence of such abnormal cell growth may change the appearance of the internal organ to be examined or resected. Further, certain patients may have different anatomical structure and may exhibit variation in positioning, size, shape, and appearance of an internal organ, for example, an abdominal organ. In certain other scenarios, the appearance of the internal organ of the patient may be different from its normal appearance due to an infection or a disease.

As a result of the complexity of the internal organs, it may be difficult to assume the appearance of the internal organ during surgery. Unless compensated suitably, it may be difficult to perform the surgery accurately and safely on the correct location of the internal organ. Thus, an improved technique and/or system may be required to reduce complexities for the surgeon, and provide safe, accurate, and quick assistance to perform the surgery with improved accuracy and safety.

Further limitations and disadvantages of conventional and traditional approaches will become apparent to one skill in the art, through comparison of described systems with some aspects of the present disclosure, as set forth in the remainder of the present application and with reference to the drawings.

SUMMARY

An apparatus and a method are provided for internal organ localization of a subject for providing assistance during surgery, as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
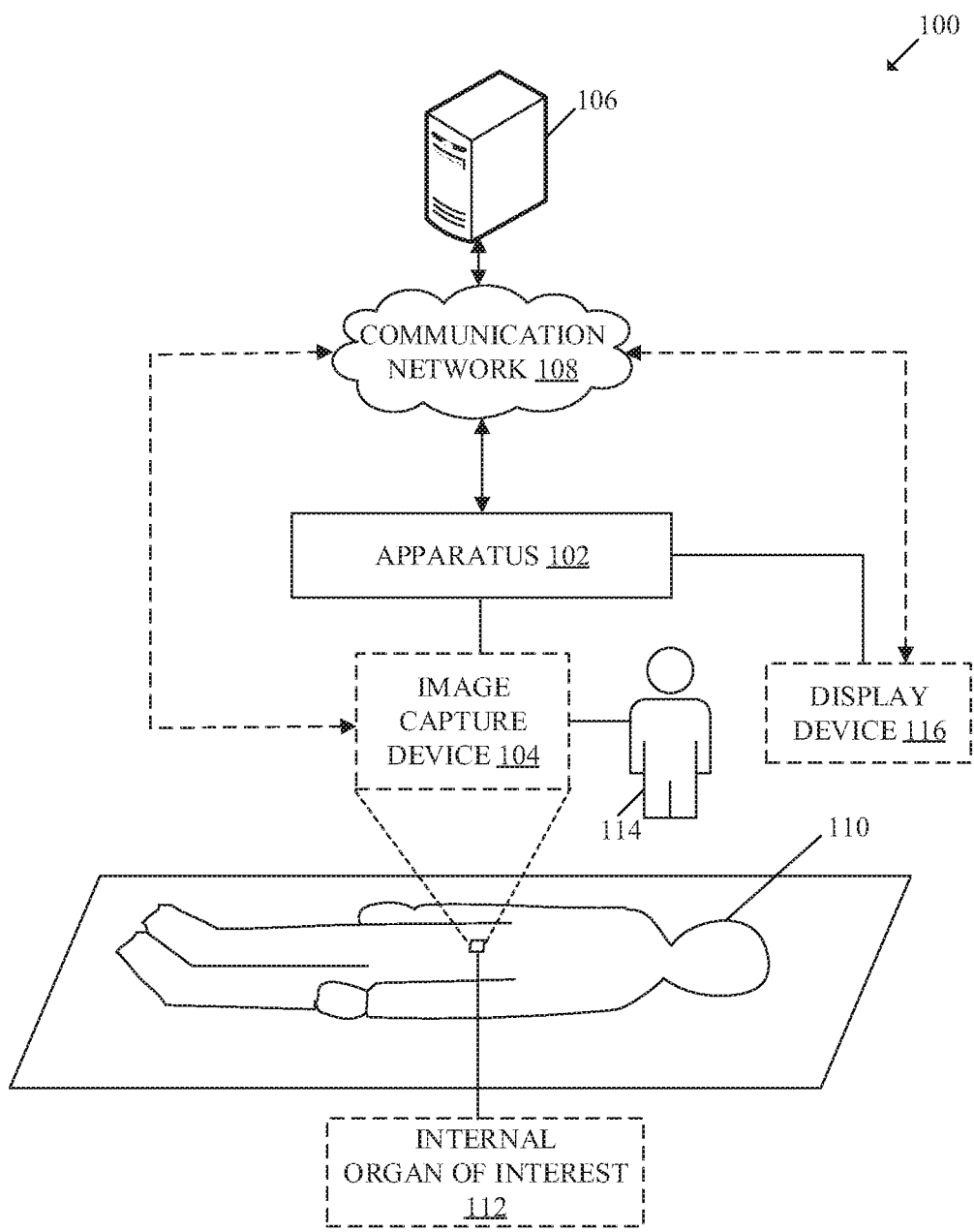
FIG. 1 is a diagram that illustrates a network environment for localization of an internal organ of a subject for providing assistance during surgery, in accordance with an embodiment of the disclosure.

Certain embodiments of the disclosure may be found in an apparatus and method for internal organ localization of a subject for providing assistance during surgery. Various embodiments of the disclosure provide an apparatus that may include an image capture device and circuitry that is communicatively coupled to the image capture device. The image capture device may be configured to capture a sequence of video frames of one or more internal organs of a subject. The capture of the sequence of video frames of the one or more internal organs of the subject may be done based on insertion of the image capture device in a body of the subject. In some embodiments, the internal organ may be an abdominal organ. The circuitry may be configured to generate test data from a test video frame selected from the captured sequence of video frames. The test data may include a plurality of patches of the test video frame. The circuitry may be further configured to compute appearance data of an internal organ of interest in the test video frame. The appearance data may be computed based on the generated test data from the test video frame and specified training data for the internal organ of interest.

In accordance with an embodiment, the circuitry may be further configured to determine orientation data of the internal organ of interest within the body of the subject. The orientation data may be estimated based on a known orientation of the image capture device and a maximum correlation of the test video frame with a specified anatomical template for the internal organ of interest. The circuitry may be further configured to generate supplement information for the internal organ of interest in the captured sequence of video frames. The supplemental information may be generated based on the computed appearance data of the internal organ of interest and the determined orientation data of the internal organ of interest. The circuitry may be further configured to localize at least a portion of the internal organ of interest within the body of the subject in the surgery, based on the generated supplemental information.

In accordance with an embodiment, the circuitry may be configured to receive the captured sequence of video frames of the one or more internal organs of the subject. The circuitry may be further configured to select the test video frame from the received sequence of video frames. Such selection of the test video frame may be done based on an area occupied by the internal organ of interest in the test video frame. The area occupied by the internal organ of interest in the test video frame may be greater than a threshold area.

In accordance with an embodiment, the circuitry may be further configured to extract a set of training patches from the specified training data by a random sampling technique. The extraction of the set of training patches may be done based on the selected test video frame. The circuitry may be further configured to utilize the selected set of training patches for estimation of the appearance data. The random sampling technique may be Monte Carlo sampling.

In accordance with an embodiment, the circuitry may be further configured to compute a color likelihood of a portion of the test video frame that includes the organ of interest. The computation of the color likelihood may be done based on a comparison of a color component of the portion of the test video frame with a color component in the extracted set of training patches of the specified training data. The circuitry may be further configured to compute a texture likelihood of a portion of the test video frame that includes the organ of interest. Such computation of the texture likelihood may be based on a comparison of a texture component of the portion of the test video frame with a texture component in the extracted set of training patches of the specified training data. The circuitry may be further configured to utilize the color likelihood and the texture likelihood that are computed independent of each other to derive an appearance likelihood of the internal organ-of-interest in the test video frame. The appearance likelihood corresponds to the estimated appearance data.

In accordance with an embodiment, the circuitry may be further configured to compute a plurality of kernel values for the known orientation of the internal organ of interest to estimate the orientation data of the internal organ of interest within the body of the subject. The circuitry may be further configured to estimate the plurality of kernel values for a portion of the test video frame that includes the organ of interest. The estimation of the plurality of kernel values may be based on a similarity of pose information in the specified anatomical template with the test video frame. The specified anatomical template of the internal organ of interest may include a reference 3D graphic model of the internal organ of interest rendered at a first orientation. The circuitry may be further configured to change an orientation of a rendering of the reference 3D graphic model of the internal organ of interest from the first orientation to a second orientation in accordance to an orientation of the internal organ of interest visible in the test video frame.

In accordance with an embodiment, the circuitry may be further configured to localize a portion occupied by the internal organ of interest of the subject within the test video frame. Such localization of the portion occupied by the internal organ of interest of the subject may be performed based on a convolution of the appearance data and the estimated plurality of kernel values.

In accordance with an embodiment, the circuitry may be further configured to compare the localized portion within the test video frame with a localized portion in different test video frames that are a part of the captured sequence of video frames received as a continuous video feed from the image capture device. The circuitry may be further configured to assign a set of markers at a contour of the localized portion of the internal organ of interest, in the test video frame and different test video frames that are a part of the captured sequence of video frames received as a continuous video feed from the image capture device. The supplemental information may include at least the assigned set of markers at the contour of the localized portion of the internal organ of interest.

In accordance with an embodiment, the circuitry may be further configured to modify the captured sequence of video frames in real time or near-real time to include the generated supplemental information in a specific portion in the captured sequence of video frames. The modification of the captured sequence of video frames in real time or near-real time may be based on the computed appearance data of the internal organ of interest and the determined orientation data of the internal organ of interest. The circuitry may be further configured to display, at a display device, the generated supplemental information in the specific portion in the modified sequence of video frames as a continuous feed captured by the image capture device, in real time or near-real time. The circuitry may be further configured to generate an instruction to enable navigation of the image capture device and a surgical instrument within the body of the subject to reach to the localized portion of the internal organ of interest.

FIG. 1 is a diagram that illustrates a network environment for localization of an internal organ of a subject for providing assistance during surgery, in accordance with an embodiment of the disclosure. With reference to FIG. 1, there is shown a network environment 100 that may include an apparatus 102, an image capture device 104, a server 106, and a communication network 108. There is further shown one or more users, such as a human subject 110, an internal organ of interest 112 of the human subject 110, and a surgeon 114. The apparatus 102 may be communicatively coupled to the image capture device 104, and the server 106, via the communication network 108. In some embodiments, the apparatus 102 may include a display device 116. In some embodiments, the apparatus 102 may be communicatively coupled to the display device 116.

The apparatus 102 may comprise suitable logic, circuitry, interfaces, and/or code that may be configured to localize an internal organ, such as the internal organ of interest 112, of the human subject 110 for providing assistance during surgery. The apparatus 102 may provide a real-time or near real-time assistance to the surgeon 114 during surgery by the localization of internal organ of interest 112 of the human subject 110 who is subjected to the surgery. Examples of the apparatus 102 may include, but are not limited to, a surgical assistive device, a computer-assisted surgical system or a robot-assisted surgical system, a medical device, an electronic surgical instrument, a display device, and/or a computing device.

In some embodiments, the apparatus 102 may further include an image capture device 104. In some embodiments, the image capture device 104 may be communicatively coupled to the apparatus 102, via a wired or wireless communication medium. The image capture device 104 may capture one or more video frames of the internal organ of interest 112 of the human subject 110 when a surgery or diagnostic procedure is performed on the internal organ of interest 112. Examples of the image capture device 104 may include, but are not limited to, a laparoscopic camera, a medical resonance imaging (MRI) device, a computer tomography (CT) scanning device, a minimally invasive medical imaging device, and/or a minimal incision medical imaging device.

The server 106 may comprise suitable logic, circuitry, interfaces, and/or code that may be configured to store one or more datasets of training data related to appearance data and specific anatomical template related to the internal organ of interest 112 to determine orientation data. The one or more datasets of the training data may correspond to the imaging data of the organ of interest, such as a liver or other abdominal organ, of different human subjects. In accordance with an embodiment, the one or more datasets of the training data may include a set of training patches of the portion of the organ of interest of different human subjects. The server 106 may be configured to store at least an anatomical template or an organ atlas to determine orientation data for the internal organ of interest 112. The anatomical template may correspond to a reference 3D graphical model of the internal organ of interest 112. The anatomical template of various internal organs of human body may correspond to high-quality computed tomography (CT) and Magnetic Resonance Imaging (MRI) scans. In accordance with an embodiment, the server 106 may be configured to provide the pre-stored one or more datasets to the apparatus 102, via the communication network 108. In accordance with an embodiment, the apparatus 102 may directly receive the one or more datasets from an external data source (not shown). In accordance with an embodiment, the apparatus 102 may directly receive a plurality of anatomical templates for a reference 3D graphical model from the external source, such as a cloud server. In accordance with an embodiment, both the server 106 and the apparatus 102 may be part of a computer-assisted surgical system. In accordance with an embodiment, the server 106 may be implemented as a plurality of cloud-based resources, a database server, a file server, an application server, a web server, and/or their combination.

A person of ordinary skill in the art will understand that the scope of the disclosure is not limited to implementation of the server 106 and the apparatus 102 as separate entities. In accordance with an embodiment, the functionalities of the server 106 may be implemented by the apparatus 102, without departure from the scope of the disclosure.

The communication network 108 may include a medium through which the apparatus 102, the image capture device 104, and/or the server 106 may communicate with each other. The communication network 108 may be a wired or wireless communication network. Examples of the communication network 108 may include, but are not limited to, a Local Area Network (LAN), a Wireless Local Area Network (WLAN), a cloud network, a Long Term Evolution (LTE) network, a plain old telephone service (POTS), a Metropolitan Area Network (MAN), and/or the Internet. Various devices in the network environment 100 may be configured to connect to the communication network 108, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

The internal organ of interest 112 may be an anatomical region, for example, an abdominal organ, of a subject, such as the human subject 110. The abdominal organ may include a liver, left kidney, right kidney, a spleen, pancreas and/or the like. The internal organ of interest 112 may include infected or diseased portion of an abdominal organ or an abdominal organ with cyst or tumor growth. In accordance with an embodiment, the internal organ of interest 112 may be an internal organ or at least a portion of the internal organ of the human subject 110 that is subject to surgery.

A person of ordinary skill in the art will understand that the scope of the disclosure is not limited to implementation of the disclosed apparatus and method to assist during surgery of the internal organ of interest 112 of the human subject 110, as shown. In accordance with an embodiment, the disclosed apparatus and method may be used to assist during surgery of at least a portion of the internal organ of interest of an animal subject. Further, the disclosed apparatus and method may also be useful to provide assistance during surgery of anatomical portions or regions other than the abdominal organs, as discussed above.

The display device 116 may comprise suitable logic, circuitry, interfaces, and/or code that may be configured to display a modified sequence of video frames such that a path to access the localized the internal organ of interest 112 within the human subject 110 is visible in real time or near-real time. The internal organ of interest 112 may be localized while the surgical or diagnostic procedure is performed on the internal organ of interest 112 or a portion of the internal organ of interest 112 of the human subject 110. Examples of the display device 116 may include, but are not limited to, a display screen, a display of a surgical apparatus, such as the apparatus 102, or other special-purpose display devices suited for surgical procedures. A person with ordinary skill in the art will understand that in accordance with an embodiment, the display device 116 may be integrated with the apparatus 102. Alternatively, the display device 116 may be communicatively coupled to the apparatus 102 and a user, such as a surgeon 114, of the display device 116 may control the apparatus 102, via a user-interface of the display device 116.

In operation, a user (e.g., the surgeon 114) may insert an image capture device 104 in a body region, such as an abdominal region, of the human subject 110. The image capture device 104 may be attached to a terminal end of an instrument, such as a laparoscope. The image capture device 104 may be a surgical grade image sensor suited to capture a sequence of video frames of internal organs of the human subject 110. The image capture device 104 may be inserted through a small incision in the body of the human subject 110. For example, the surgeon 114 may want to find where an internal organ of interest 112 is present or located inside the body of the human subject 110 for computer assisted navigation. The internal organ of interest may be an abdominal organ, for example, a liver, which the surgeon 114 may want to precisely locate in a laparoscopic surgery. In some embodiments, the internal organ of interest may include, but are not limited to pancreas, spleen, kidneys, and the like.

In certain scenarios, the internal organ that has to be examined or resected, may not be clearly visible to the surgeon 114 because of the presence of blood, gases, tissues that may lie in the field of view of a surgical instrument or the image capture device 104 during surgery. Further, a view of internal organ of interest 112 may be blocked by tumor growth on the same organ or neighboring organs. In certain cases, abnormal cell growth may change the structure of appearance of the internal organ of interest 112 that has to be examined or resected. Further, it is observed that certain patients may have different anatomical structures, exhibiting variation in the positioning, size, and shape, appearance of the abdominal organ. In certain other scenarios, the appearance of the organ of interest 112 of the human subject 110 may be changed due to an infection and a disease. As a result of the complexity of the internal organs, it may be difficult to assume same appearance of the internal organ of interest 112 during surgery. Further, it may be difficult for the surgeon 114 to accurately and safely perform the surgery on the correct location of the internal organ of interest 112. The apparatus 102 reduces such complexities for the surgeon 114, and provides safe, accurate, and quick assistance to perform surgery with improved accuracy and safety.

In the operative stage, the image capture device 104 may be configured to capture a sequence of video frames (e.g., a video) that includes a portion of one or more internal organs of the human subject 110. The apparatus 102 may be configured to receive the captured sequence of video frames from the image capture device 104. As the captured sequence of video frames may include different internal organs of the human subject 110, certain images may be selected from the captured sequence of video frames for further processing to avoid selection of unwanted image frames where a view of the internal organ of interest may not be present or a quality score of the view may be less than a threshold quality as a result of presence of other anatomical portion of the human subject 110. The apparatus 102 may be configured to select a test video frame from the received sequence of video frames. Such selection of the test video frame may be based on an area occupied by the internal organ of interest 112 in the test video frame. The test video frame may be selected when the area occupied by the internal organ of interest 112 in the test video frame may be greater than a threshold area.

The apparatus 102 may be configured to generate test data from the test video frame selected from the captured sequence of video frames. The test data may include a plurality of patches of the test video frame. The apparatus 102 may be configured to receive at least a set of training patches from the dataset that includes a specified training data associated with the internal organ of interest 112 from the server 106. The set of training patches from the dataset may include image patches extracted from a plurality of two dimensional (2D) images that represents the surface of the internal organ of interest 112 taken in pre-operative stage or representative 2D images of same internal organ of interest of different individuals. In some embodiments, the set of training patches from the dataset may include the patches extracted from multi-modal images. The multi-modal images may correspond to data taken from Magnetic Resonance Imaging (MRI), Computed Tomography (CT), Positron emission tomography (PET), Fluid-attenuated inversion recovery (FLAIR), and Magnetic Resonance Angiography (MRA) based medical imaging techniques. The specified training data may include a set of training patches that may correspond to the organ of interest 112. The apparatus 102 may be configured to retrieve the set of training patches from the specified training data by a random sampling technique based on the selected test video frame. The random sampling technique may be a Monte Carlo sampling. However, other sampling techniques may also be used without limiting the scope of the disclosure. The apparatus 102 may be further configured to utilize the selected set of training patches for estimation of the appearance data.

The apparatus 102 may be further configured to compute a color likelihood of a portion of the test video frame that includes the internal organ of interest 112. The computation of the color likelihood of the portion of the test video frame may be done based on a comparison of a color component of the portion of the test video frame with a color component in the extracted set of training patches of the specified training data. The color component may correspond to an RGB color model. The apparatus 102 may be further configured to compute a texture likelihood of a portion of the test video frame that includes the internal organ of interest 112. The computation of the texture likelihood of the portion of the test video frame may be done based on a comparison of a texture component of the portion of the test video frame with a texture component in the extracted set of training patches of the specified training data. The color likelihood and the texture likelihood may be computed independent of each other to derive an appearance likelihood of the internal organ of interest 112 in the test video frame. The appearance likelihood corresponds to the appearance data of the internal organ of interest 112 in the test video frame. Alternatively stated, the apparatus 102 may be configured to compute appearance data of the internal organ of interest 112 in the test video frame. Such computation of the appearance data may be done from test data generated from the test video frame and the specified training data for the internal organ of interest 112. The computed appearance data may correspond to an estimated appearance likelihood of the internal organ of interest 112 in the test video frame.

In accordance with an embodiment, the apparatus 102 may be further configured to determine orientation data of the internal organ of interest 112 within the human subject 112. In accordance with an embodiment, the apparatus 102 may be configured to extract a specific anatomical template for the internal organ of interest 112 from the server 106 to determine orientation data. The orientation data may be estimated based on a known orientation of the image capture device 104 and a maximum correlation of the test video frame with a specified anatomical template for the internal organ of interest.

The apparatus 102 may be further configured to compute a plurality of kernel values for the known orientation of the image capture device 104. The known orientation of the image capture device 104 corresponds to a current pose of the image capture device 104, for example, laparoscope pose, which is further utilized to localize the internal organ of interest 112 (e.g., an abdominal organ during laparoscopic surgery) as posterior probability. The pose of the image capture device 104 may be priori information. The prior and posterior computation is further described in details, for example, in FIGS. 3A, 3B, and 3C. In accordance with an embodiment, the plurality of kernel values may be estimated using a defined convolution matrix, based on a similarity of pose information of a 3D graphic model of the internal organ of interest 112 in the specified anatomical template, with current orientation of the internal organ of interest 112 in the test video frame. The specified anatomical template of the internal organ of interest 112 includes the reference 3D graphic model of the internal organ of interest 112 rendered at a first orientation. The apparatus 102 may be further configured to change an orientation of a rendering of the reference 3D graphic model of the internal organ of interest 112 from the first orientation to a second orientation in accordance to an orientation of the internal organ of interest 112 visible in the test video frame. Accordingly, the maximum correlation of the test video frame with a specified anatomical template for the internal organ of interest 112 may be estimated.

In accordance with an embodiment, the apparatus 102 may be further configured to localize at least a portion of the internal organ of interest 112 within the body of the human subject 110 in the surgery. The apparatus 102 may be further configured to localize a portion occupied by the internal organ of interest 112 of the human subject 110 within the test video frame. Such localization of the portion occupied by the internal organ of interest 112 of the human subject 110 may be based on a convolution of the appearance data and the estimated plurality of kernel values. The apparatus 102 may be configured to utilize a Bayesian framework for computation of localization of the portion of the internal organ of interest 112. The apparatus 102 may be further configured to compare the localized portion within the test video frame with a localized portion in different test video frames that are a part of the captured sequence of video frames received as a continuous video feed from the image capture device 104.

The apparatus 102 may be further configured to assign a set of markers at a contour of the localized portion of the internal organ of interest 112, in the test video frame and different test video frames that are a part of the captured sequence of video frames received as a continuous video feed from the image capture device 104. The supplemental information may include at least the assigned set of markers at the contour of the localized portion of the internal organ of interest. The apparatus 102 may be further configured to modify the captured sequence of video frames in real time or near-real time to include the generated supplemental information in a specific portion in the captured sequence of video frames. The modification of the captured sequence of video frames in real time or near-real time may be based on the computed appearance data of the internal organ of interest and the determined orientation data of the internal organ of interest 112 of the human subject 110.

The apparatus 102 may be further configured to display, at a display device 116, the generated supplemental information in the specific portion in the modified sequence of video frames as a continuous feed captured by the image capture device 104, in real time or near-real time. The apparatus 102 may be further configured to generate an instruction to enable navigation of the image capture device 104 or a surgical instrument within the body of the human subject 110 to reach to the localized portion of the internal organ of interest 112.

Figure 2:
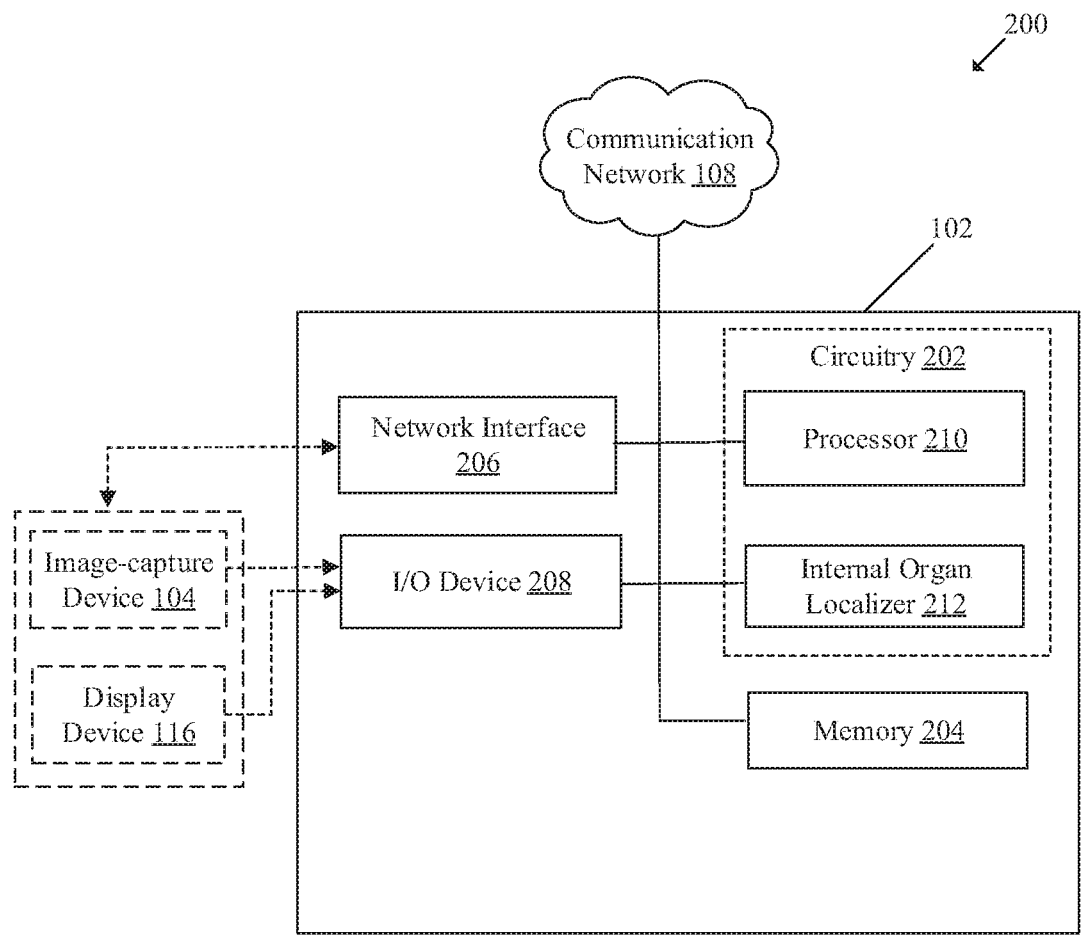
FIG. 2 illustrates a block diagram of an exemplary apparatus for localization of an internal organ of a subject for providing assistance during surgery, in accordance with an embodiment of the disclosure.

FIG. 2 illustrates a block diagram of an exemplary apparatus for localization of an internal organ of a subject for providing assistance during surgery, in accordance with an embodiment of the disclosure. FIG. 2 is explained in conjunction with elements from FIG. 1. With reference to FIG. 2, there is shown the apparatus 102. The apparatus 102 may comprise a plurality of circuits, such as circuitry 202, a memory 204, a network interface 206, and one or more input/output (I/O) devices, such as an I/O device 208. The circuitry 202 may comprise a processor 210 and an internal organ localizer 212. The I/O device 208 may be communicatively coupled to the image capture device 104 and the display device 116, via a wired or wireless communication medium.

The circuitry 202 may be communicatively coupled to the memory 204, the network interface 206, and the I/O device 208. The network interface 206 may communicate with one or more servers, such as the server 106, via the communication network 108 under the control of the circuitry 202.

The memory 204 may comprise suitable logic, circuitry, and/or interfaces that may be configured to store a set of instructions executable by the circuitry 202. The memory 204 may be configured to store one or more datasets of training data related to appearance data and specific anatomical template corresponding to the internal organ of interest 112. Alternatively, the one or more datasets may be stored at the server 106. In accordance with an embodiment, the memory 204 may be further configured to temporally store the one or more video frames captured by the image capture device 104. The memory 204 may be further configured to store operating systems and associated applications. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The network interface 206 may comprise suitable logic, circuitry, interfaces, and/or code that may be configured to communicate with the image capture device 104, the server 106, and/or the display device 116 via the communication network 108 (as shown in FIG. 1). The network interface 206 may implement known technologies to support wired or wireless communication of the apparatus 102 with the communication network 108. The network interface 206 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The I/O device 208 may comprise suitable logic, circuitry, interfaces, and/or code that may be configured to receive an input from and provide an output to a user, such as the surgeon 114. The I/O device 208 may include an input from the image capture device 104 and an output from the display device 116 that may be configured to facilitate a communication between the apparatus 102 and the user, such as the surgeon 114. Examples of the input devices may include, but are not limited to, the image capture device 104, a touch screen, a camera, a keyboard, a mouse, a joystick, a microphone, a motion sensor, a light sensor, and/or a docking station. Examples of the output devices may include, but are not limited to, the display device 116, a projector screen, and/or a speaker.

The processor 210 may comprise suitable logic, circuitry, interfaces, and/or code that may be configured to execute a set of instructions stored in the memory 204. Examples of the processor 210 may be an X86-based processor, X86-64-based processor, an Application-Specific Integrated Circuit (ASIC) processor, a central processing unit (CPU), an Explicitly Parallel Instruction Computing (EPIC) processor, a Very Long Instruction Word (VLIW) processor, and/or other processors or circuits.

The internal organ localizer 212 may comprise suitable logic, circuitry, interfaces, and/or code that may be configured to localize at least a portion of the internal organ of interest 112 within the body of the human subject 110 in the surgery, based on supplemental information. The internal organ localizer 212 may be configured to utilize Bayesian Framework for localization of the internal organ of interest 112 of the human subject 110. Various operations of the different components of the apparatus 102, may be further understood in details, for example, from FIGS. 3A to 3C, 4A, and 4B.

Figure 3A:
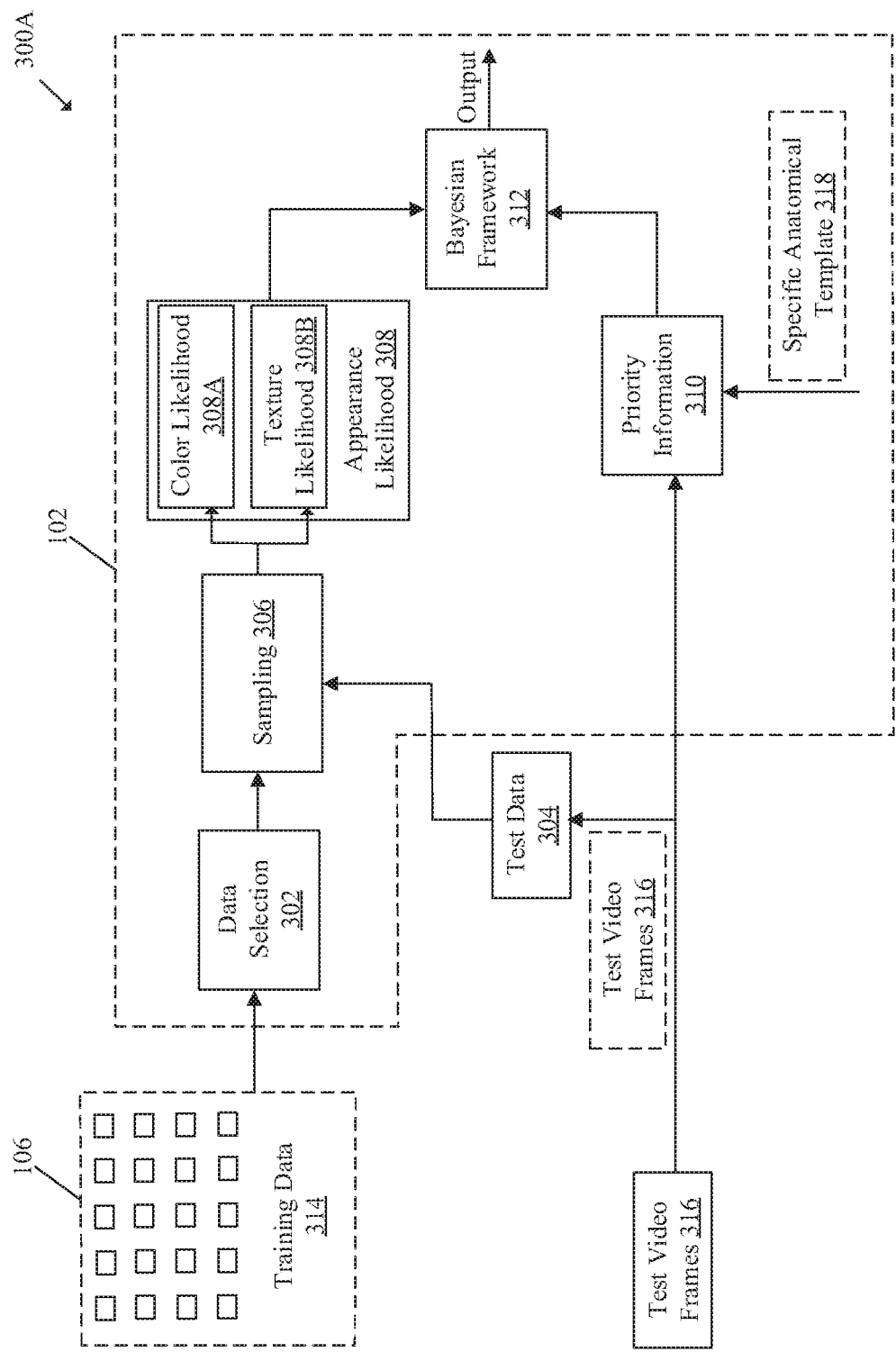
FIG. 3A, FIG. 3B, and FIG. 3C, collectively, illustrate an exemplary scenario for implementation of the apparatus and method for localization of an abdominal organ of a subject for providing assistance during surgery, in accordance with an embodiment of the disclosure.
Figure 3B:
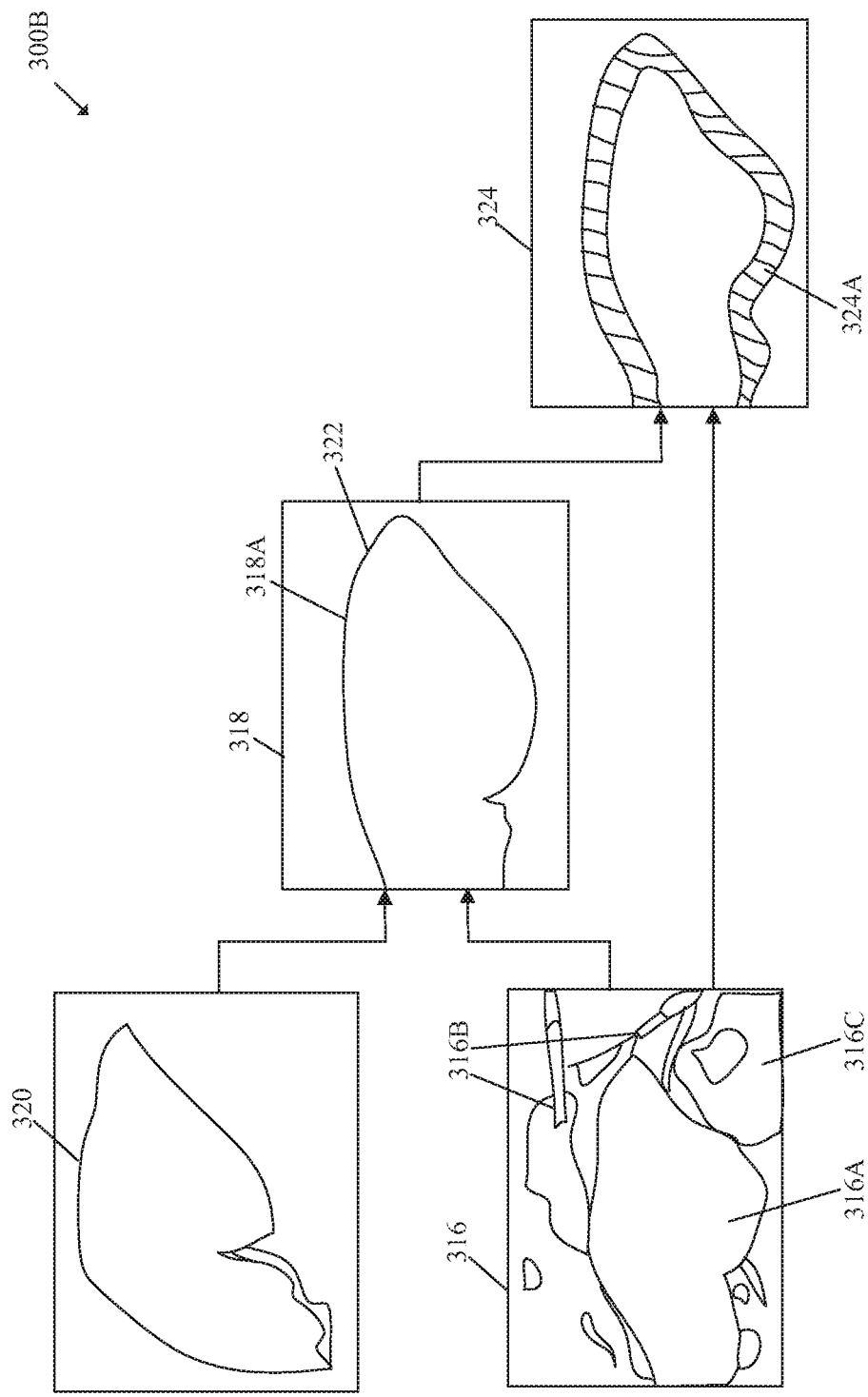
Figure 3C:
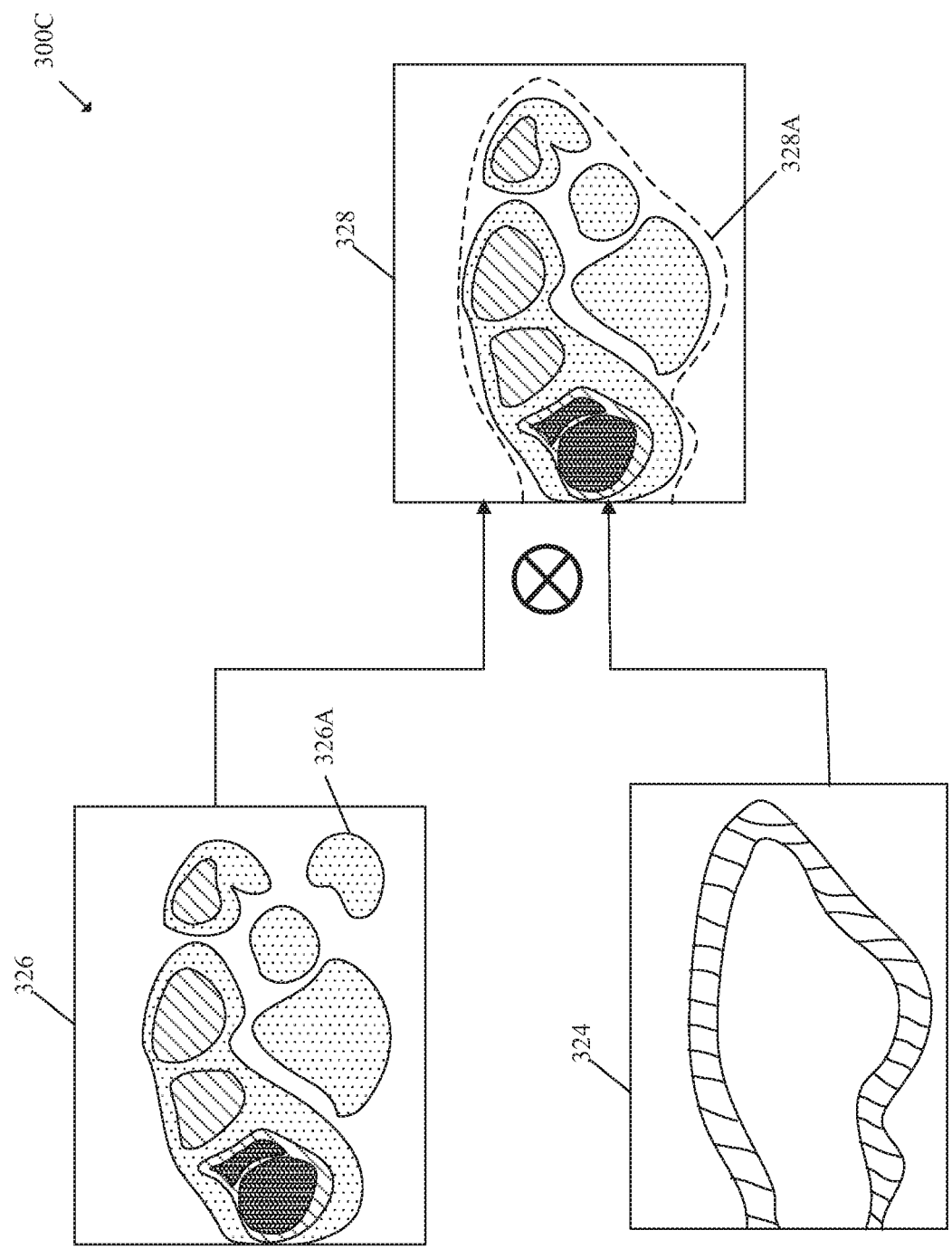

FIG. 3A, FIG. 3B, and FIG. 3C, collectively, illustrate an exemplary scenario for implementation of the apparatus and method for localization of an abdominal organ of a subject for providing assistance during surgery, in accordance with an embodiment of the disclosure. With reference to FIG. 3A, there is shown a scenario 300A to depict a processing pipeline for localization of an abdominal organ, such as a liver, of a subject, during surgery (e.g., hepatectomy in this case). FIG. 3A is explained in conjunction with elements from FIG. 1 and FIG. 2. In FIG. 3A, there is shown different operations 302, 306, 308, and 312 in the processing pipeline. There is also shown various input, for example, training data 314, a test video frame 316, test data 304, a specific anatomical template 318, and priori information 310, provided at different stages of the processing pipeline.

At 302, data selection may be done by selection of training data 316 related to liver. The liver may correspond to the internal organ of interest 112 of the human subject 110. Data selection may be done to train a learning engine (not shown) in the memory 204 for a prior appearance of the liver. The training data 314 may include at least a set of training patches that represents appearance of the liver. In accordance with the exemplary scenario, the training data 314 may correspond to one or more datasets of imaging data of one or more portions of liver of different human subjects. The processor 210 may be configured to extract the training data 316 from the memory 204 or the server 106. The set of training patches from the dataset may include the patches extracted from multi-modal images, for example, images taken from the Magnetic Resonance Imaging (MRI), the Computed Tomography (CT), the Positron emission tomography (PET), the Fluid-attenuated inversion recovery (FLAIR) and the Magnetic Resonance Angiography (MRA) based medical imaging techniques for the same or a different human subject previously.

At 304, test data may be generated from the test video frame 316. The image capture device 104, such as a laparoscope, may be configured to capture a sequence of video frames (e.g., a video) of one or more abdominal organs. The captured sequence of video frames may include a portion of one or more abdominal organs of the human subject 110. In accordance with an embodiment, the I/O device 208 may be configured to receive the captured sequence of video frames from the image capture device 104. The captured sequence of video frames may include different internal organs of the human subject 110. Therefore, certain images may be selected from the captured sequence of video frames for further processing to avoid selection of unwanted image frames where a view of the liver may not be present or a quality score of the view may be less than a threshold quality as a result of presence of other anatomical portion of the human subject 110. The processor 210 may be configured to select one or more test video frames, such as the test video frame 316, from the received sequence of video frames. Such selection of the test video frame 316 may be based on an area occupied by the liver in the test video frame 316. The test video frame 316 may be selected when the area occupied by the liver in the test video frame 316 may be greater than a threshold area. The processor 210 may be configured to generate test data 304 from the test video frame 316 selected from the captured sequence of video frames. The test data 304 may include a plurality of patches of the test video frame 316 captured at surgery in real time of near-real time.

At 306, sampling may be done. The processor 210 may be configured to receive the set of training patches from the training data 316 corresponding to the liver by a random sampling technique based on the test data 304 from the test video frame 316. The test video frame 316 may be a high-resolution video frame. Further, the set of training patches may be large in number, for example, taken from thousands of sample images. The high resolution video frames and the large number of training data may increase computational load on the processor 210. Therefore, to decrease the computational load on the processor 210, a random sampling technique may be performed. The random sampling technique may be a Monte Carlo sampling. However, other sampling techniques may also be used without limiting the scope of the disclosure. The processor 210 may be further configured to utilize the received set of training patches for estimation of the appearance data.

At 308, appearance likelihood may be computed. The internal organ localizer 212 may receive the training patches after the sampling technique performed on the training patches. In accordance with an embodiment, the size of the training patches may be defined to reduce computational load, for example, a patch of 128 by 128 pixels may be selected. The appearance of the liver may be modelled probabilistically by computation of appearance likelihood. The appearance likelihood of the liver may be computed by computation of color likelihood and texture likelihood of the liver independently by using the training data 314.

The internal organ localizer 212 may be configured to compute appearance data of the liver (an internal organ of interest) in the test video frame 316, where the appearance data may correspond to an appearance likelihood. Such computation of the appearance data may be based on the generated test data 304 from the test video frame 316 and the sampled training patches of the training data 316 for the liver. The appearance likelihood 308 may be estimated by computing a color likelihood 308A and a texture likelihood 308B of the liver in the test data 304 from the test video frame 316. The color likelihood 308A and the texture likelihood 308B of the liver may be computed independent of each other. Therefore, the appearance likelihood 308 may be based on prior information that is how a liver looks like in terms of color and texture.

The computation of the color likelihood 308A of a portion of the test video frame that includes the liver may be done based on a comparison of a color component of the portion of the test video frame with a color component in the extracted set of training patches of the training data 314. The color component may correspond to an RGB color model. The internal organ localizer 212 may be further configured to compute the texture likelihood 308B of a portion of the test data 304 of the test video frame 316 that includes the liver. The computation of the texture likelihood 308B of the portion of the test video frame may be done based on a comparison of a texture component of the portion of the test video frame 316 with a texture component in the extracted set of training patches of the training data 314. The color likelihood 308A and the texture likelihood 308B may be computed independent of each other to derive the appearance likelihood 308 of the liver (i.e., the internal organ of interest) in the test video frame 316.

In accordance with an embodiment, the appearance likelihood 308 may also be calculated in terms of probability by calculating color probability and texture probability of the liver. To calculate the appearance probability, the color probability may be multiplied with texture probability. Therefore, the likelihood function from appearance may be represented by the equation (1), as given below:

$$P(A|Lx) = P(C|Lx) \cdot P(T|Lx) \tag{1}$$

Where P (C|Lx) represents probability of color of liver "L" at "x" coordinate.
P (T|Lx) represents probability of texture of liver "L" at "x" coordinate.
P (A|Lx) represents probability of appearance of liver "L" at "x" coordinate.

At 310, priori information may be determined and fed to the Bayesian framework. The internal organ localizer 212 may be configured to determine priori information by determining orientation data of the liver of the human subject 112. To determine the priori information 310, the specific anatomical data 318 of the liver and the test video frame 316 may be used. The specific anatomical template 318 may correspond to a reference 3D graphical model of the liver. In some embodiments, the anatomical template may be stored templates of the liver and may correspond to high-quality CT (computed tomography) and MRI (Magnetic Resonance Imaging) scans.

In accordance with an embodiment, the internal organ localizer 212 may be configured to receive the specific anatomical template 318 for the liver from the server 106. The orientation data of the liver may be estimated based on a known orientation of the image capture device 104 and a maximum correlation of the test video frame 316 with the specific anatomical template 318 for the liver (i.e., the internal organ of interest). The internal organ localizer 212 may be further configured to compute a plurality of kernel values for the known orientation of the image capture device 104. The plurality of kernel values may be estimated for a portion of the test video frame 316 that includes the liver. The kernel values may correspond to values present in a convolution matrix (also referred to as a kernel matrix/kernel). Different convolution matrices may be utilized to generate a type of effect on the image, through execution of specific operations, such as edge detection, line detection, image blurring, and image sharpening. Such estimation of the plurality of kernel values may be done based on a similarity of pose information in the specific anatomical template 318 with the test video frame 316.

The specific anatomical template 318 of the liver may include a reference 3D graphic model of the liver rendered at a first orientation. The internal organ localizer 212 may be further configured to change an orientation of a rendering of the reference 3D graphic model of the liver from the first orientation to a second orientation in accordance to an orientation of the liver visible in the test video frame 316. Accordingly, the maximum correlation of the test video frame 316 with the specific anatomical template 318 for the liver may be estimated. The estimated correlation may be used as the priori information.

The priori information for orientation estimation may be represented by equation (2), as given below:

$$P(Lx|u) = \frac{1}{\sqrt{2\pi} f\theta_\sigma} \chi_{R_L} * \exp\left(-\frac{|y|^2}{2(f\theta)^2}\right) \quad (2)$$

Where P (Lx|u) represents probability of liver for orientation prior;
$\theta_\sigma$ represents orientation uncertainty;
y, f, u represents an indicator function, a focal length, an orientation of the image capture device 104 respectively;
$\chi_{R_L}$
For example, if $f\theta_\sigma=40$, that is if the focal length (f) of the image capture device 104 is large, the uncertainty may increase, i.e., the liver (the internal organ of interest) may be too far from the image capture device 104 (such as the laparoscope).
"y" which is the indicator function, may be used for convolution with an uncertainty Gaussian of the image capture device 104. An anatomical template or organ atlas of a human body may be used to calculate the value of indicator function, e.g., the indicator function=1 for the liver area. If there is zero (i.e., no) uncertainty for position of an internal organ of interest (such as the liver), then a mask of the indicator function around that internal organ of interest may be generated. If there is some uncertainty about position of internal organ of interest (such as the liver in this case), then a boundary of the internal organ of interest may be expanded slightly by convolution. Convolution may be done by multiplying color value of pixels of the internal organ of interest (such as the liver), around the boundary and color value of neighboring pixels using a defined matrix. The probability of the liver as a co-ordinate may be calculated by equation 2, based on, the current orientation (u) of the image capture device 104. The area occupied by the liver in the test video frame 316 may be classified as "L" at "x" coordinate, where "x" may be the centroid position of the area occupied by the liver. Therefore, the liver may be localized at Lx.

At 312, the appearance likelihood 308 and the priori information 310 is fed to the Bayesian framework. The Bayesian framework may model the liver appearance (from equation 1) and the orientation of the image capture device 104 (from equation 2) to localize the liver. In accordance with an embodiment, the internal organ localizer 212 may be configured to localize at least a portion of the liver (i.e., the internal organ of interest) within the body of the human subject 110 in the surgery. Such localization may be done using supplemental information. For example, the internal organ localizer 212 may be further configured to localize a portion occupied by the liver of the human subject 110 within the test video frame 316. Such localization of the portion occupied by the liver of the human subject 110 may be done based on a convolution of the appearance data and the estimated plurality of kernel values for orientation data. Therefore, posterior probability of localization of liver into a Bayesian framework may be calculated by multiplying probability of prior appearance and probability of prior orientation by equation (3), as given below. The multiplication may be performed by the convolution process.

$$P(L_x|A,u) \propto P(A|L_x,u)P(L_x|u) \quad (3)$$

where P (Lx|A, u) may represent posterior probability of localization of liver 'L";
P (A|Lx, u) may represent probability of appearance of liver at coordinate "x"; and
P (Lx|u) may represent probability of liver at coordinate "x" with prior orientation.

The posterior probability of localization of liver 'L" may be the revised probability that is obtained after taking into consideration updated prior probability, such as the prior information 310 and the prior appearance of the appearance likelihood 308, using Bayesian framework 312.

The internal organ localizer 212 may be further configured to compare the localized portion within the test video frame 316 with a localized portion in different test video frames that are a part of the captured sequence of video frames received as a continuous video feed from the image capture device 104. The internal organ localizer 212 may be further configured to assign a set of markers at a contour of the localized portion of the liver (i.e., the internal organ of interest), in the test video frame 316 and different subsequent test video frames that are a part of the captured sequence of video frames received as a continuous video feed from the image capture device 104. The supplemental information may include at least the assigned set of markers at the contour of the localized portion of the liver. The internal organ localizer 212 may be further configured to modify the captured sequence of video frames in real time or near-real time to include the generated supplemental information in a specific portion in the captured sequence of video frames, based on the computed appearance data of the liver and the determined orientation data of the liver. The internal organ localizer 212 may be further configured to control display, at a display device 116, of the generated supplemental information in the specific portion in the modified sequence of video frames as a continuous feed captured by the image capture device 104, in real time or near-real time. The internal organ localizer 212 may be further configured to generate an instruction to enable navigation of the image capture device 104 or a surgical instrument within the body of the human subject 110 to reach to the localized portion of the liver.

FIG. 3B illustrates determination of orientation data of the liver within a body of a subject based on a specific anatomical template, in the exemplary scenario in accordance with an embodiment of the disclosure. FIG. 3B is explained in conjunction with elements from FIGS. 1, 2, and 3A. With reference to FIG. 3B, there is shown a schematic view 300B for determination of the orientation data by using the specific anatomical template 318, at surgery. There is further shown the specific anatomical template 318 that includes a reference 3D graphic model 318A of the liver at a first orientation 320 and a second orientation 322. There is also shown the test video frame 316 that depicts one or more abdominal organs, such as a liver portion 316A, a portion 316B of surgical tools, and other abdominal organ, such as a portion 316C of neighboring abdominal organ. There is further shown a representation of a convolved image 324 that acts as the priori information 310. A patterned region 310A is also shown in the convolved image 324.

The orientation data of the liver (i.e., the internal organ of interest) within the human subject 110 may be estimated based on a known orientation (u) of the image capture device 104 (such as the laparoscope at the time of surgery) and a maximum correlation of the test video frame 316 with the specific anatomical template 318 for the liver. The specific anatomical template 318 of the liver may include the reference 3D graphic model 318A of the liver initially rendered at the first orientation 320. The internal organ localizer 212 may be configured to change an orientation of a rendering of the reference 3D graphic model 318A of the liver from the first orientation 320 to the second orientation 322 in accordance to an orientation of the liver (such as the liver portion 316A) visible in the test video frame 316. Accordingly, the maximum correlation of the test video frame 316 with the specific anatomical template 318 for the liver may be estimated. Based on the convolution of the reference 3D graphic model 318A of the liver rendered at the second orientation 322 and the test video frame 316, the convolved image 324 for the liver may be obtained. A convolved region in the convolved image 324 is represented by the patterned region 310A. Convolution may modify the spatial frequency characteristics of the test video frame 316 with respect to the reference 3D graphic model of the liver rendered at the second orientation 322. The convolved image 324 may be fed as the priori information 310 to the Bayesian framework 312.

FIG. 3C illustrates localization of the liver by use of the Bayesian framework in the exemplary scenario, in accordance with an embodiment of the disclosure. FIG. 3C is explained in conjunction with elements from FIGS. 1, 2, 3A, and 3B. With reference to FIG. 3C, there is shown a representation image of appearance likelihood 326, the convolved image 324 that represents the priori information 310, and a convolved image 328 for the liver. The representation image of appearance likelihood 326 includes a patch 324A. The convolved image 328 may be localized by a boundary 328A.

The internal organ localizer 212 may be configured to localize at least a portion of the liver within the body of the human subject 110 in the surgery. The internal organ localizer 212 may be further configured to localize a portion (such as the liver portion 316A) occupied by the liver of the subject within the test video frame 316. Such localization of the portion occupied by the liver of the human subject 110 may be done based on a convolution of the appearance data of liver (in the representation image of appearance likelihood 326) and the convolved image 324 (that also acts as priori information 310) from the determined orientation data of the liver. After convolution, the convolved image 328 may be obtained as output from the Bayesian framework 312 that indicate a correct localization of the liver by removal of erroneously identified parts or regions in the representation image of appearance likelihood 326. For example, the patch 324A in the representation image of appearance likelihood 326 may be removed in the convolved image 328. The liver may be localized by the boundary 328A.

In accordance with an embodiment, the priori information 310 and the computed appearance likelihood (e.g., the representation image of appearance likelihood 326) may be fed into a Bayesian framework to localize the liver. The Bayesian framework may be utilized by the internal organ localizer 212 for computation of the location of the liver within the human subject 110. The internal organ localizer 212 may be further configured to compare the localized portion within the test video frame 316 with a localized portion in different test video frames that are a part of the captured sequence of video frames received as a continuous video feed from the image capture device 104. The internal organ localizer 212 may be further configured to assign a set of markers (not shown in figures) at a contour of the localized portion of the internal organ of interest, in the test video frame 316 and different test video frames that are a part of the captured sequence of video frames received as a continuous video feed from the image capture device.

Figure 4A:
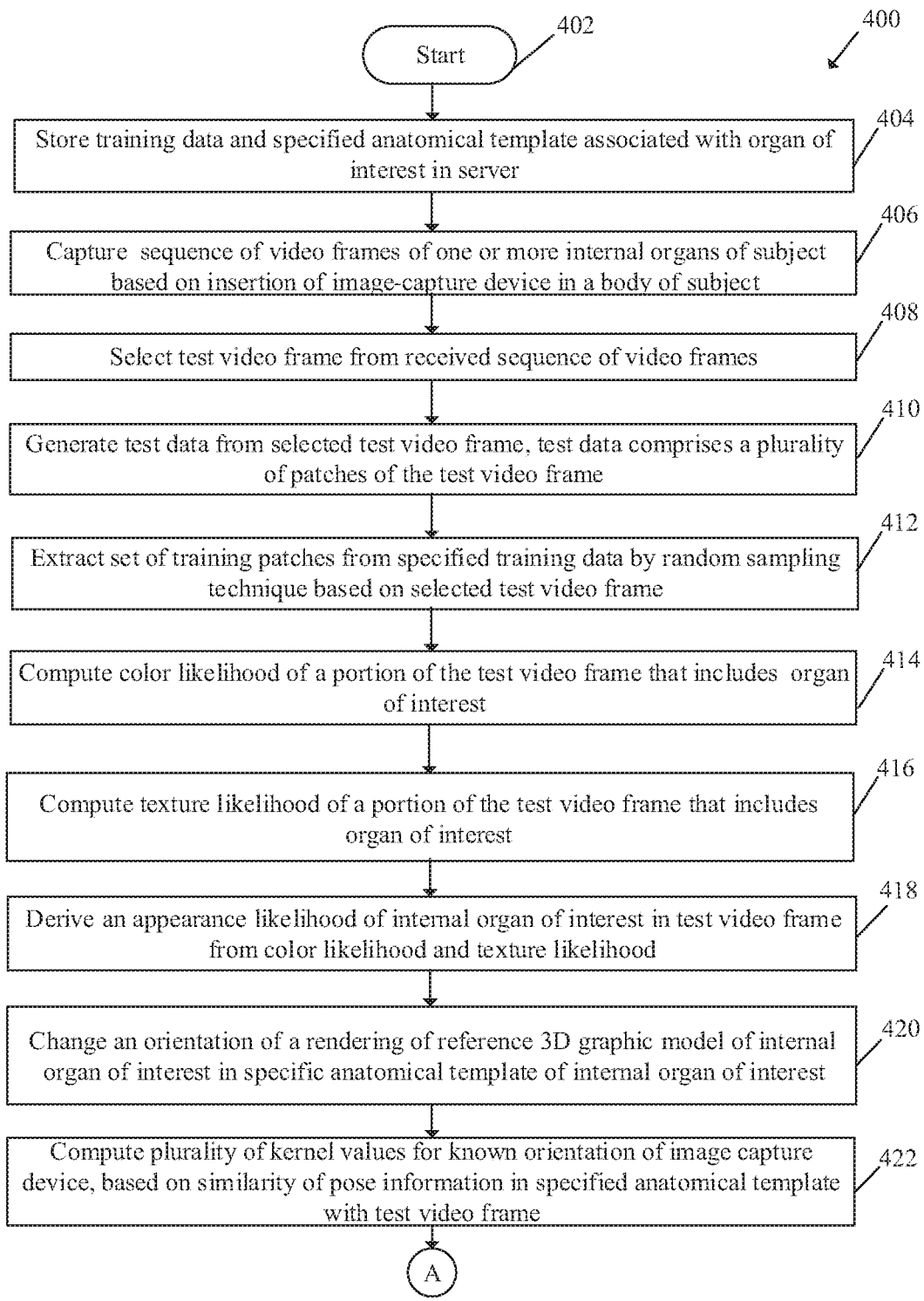
FIG. 4A and FIG. 4B, collectively illustrate a flow chart that depicts exemplary operations for internal organ localization of a subject for providing assistance during surgery, in accordance with an embodiment of the disclosure.
Figure 4B:
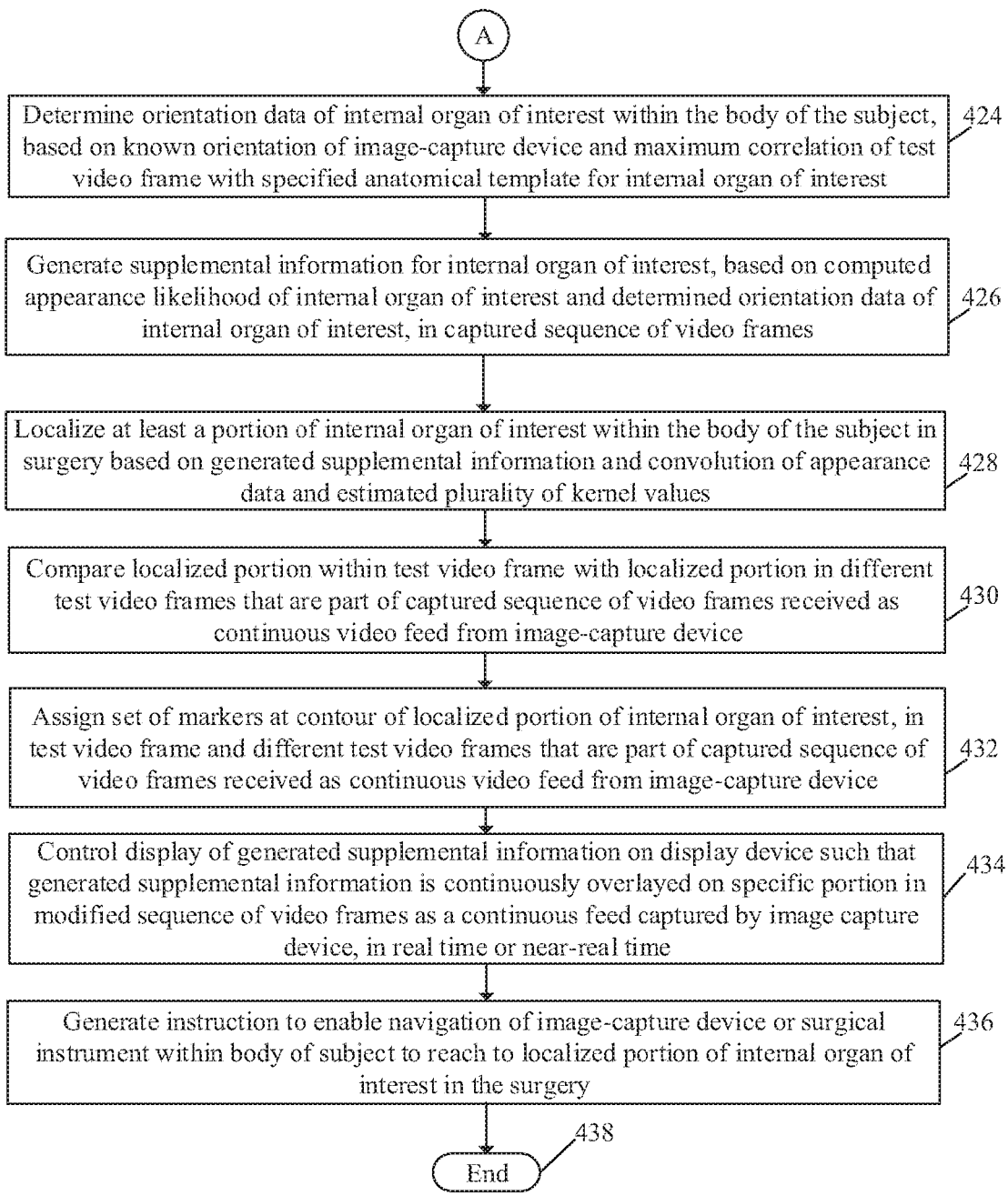

FIG. 4A and FIG. 4B, collectively, illustrate a flowchart to depict exemplary operations for localization of an internal organ of a subject to provide assistance during surgery, in accordance with an embodiment of the disclosure. With reference to FIG. 4A, there is shown a flowchart 400. The flowchart 400 is described in conjunction with elements from FIGS. 1, 2, and 3A to 3C. The method, in accordance with the flowchart 400, may be implemented in the apparatus 102. The method starts at 402 and proceeds to 404.

At 404, training data (e.g., the training data 314) and a specific anatomical template (e.g., the specified anatomical template 318) associated with the organ of interest 112 may be stored in the server 106. The specified anatomical template of the internal organ of interest 112 may include a reference 3D graphic model of the internal organ of interest rendered at a first orientation (such as the first orientation 320). At 406, a sequence of video frames of one or more internal organs of a subject (e.g., the human subject 110) may be captured based on insertion of the image capture device 104 in a body of the subject.

At 408, a test video frame (e.g. the test video frame 316) from the received sequence of video frames may be selected. The selection may be done based on an area occupied by the internal organ of interest 112 (e.g., the liver) in the test video frame. The area occupied by the internal organ of interest 112 in the test video frame may be greater than a threshold area. At 410, test data (e.g., test data 304) may be generated from the test video frame selected from the captured sequence of video frames. The test data may comprise a plurality of patches of the test video frame.

At 412, a set of training patches may be extracted from the specified training data by a random sampling technique based on the selected test video frame. The set of training patches may be utilized for estimation of the appearance data. At 414, a color likelihood of a portion of the test video frame that includes the organ of interest 112 may be computed. The color likelihood may be computed based on a comparison of a color component of the portion of the test video frame with a color component in the extracted set of training patches of the specified training data.

At 416, a texture likelihood of a portion of the test video frame that includes the organ of interest 112 may be computed. The texture likelihood may be computed based on a comparison of a texture component of the portion of the test video frame with a texture component in the extracted set of training patches of the specified training data. At 418, an appearance likelihood of the internal organ of interest 112 in the test video frame may be derived from the color likelihood and the texture likelihood. The color likelihood and the texture likelihood may be computed independent of each other to derive the appearance likelihood. The appearance likelihood may correspond to appearance data computed for the internal organ of interest 112 in the test video frame, based on the generated test data from the test video frame and specified training data for the internal organ of interest.

At 420, an orientation of a rendering of the reference 3D graphic model of the internal organ of interest 112 in the specific anatomical template of the internal organ of interest 112 may be changed from the first orientation to a second orientation. The change from the first orientation to the second orientation may occur in accordance to an orientation of the internal organ of interest 112 visible in the test video frame. At 422, a plurality of kernel values may be computed for the known orientation of the image capture device 104. The plurality of kernel values may be estimated for a portion of the test video frame that includes the organ of interest 112, based on a similarity of pose information in the specified anatomical template with the test video frame.

At 424, the orientation data of the internal organ of interest 112 may be determined within the body of the human subject 10, based on a known orientation of the image capture device 104 and a maximum correlation of the test video frame with the specified anatomical template for the internal organ of interest 112. At 426, supplemental information for the internal organ of interest 112 may be generated, based on the computed appearance likelihood (i.e., appearance data) of the internal organ of interest 112 and the determined orientation data of the internal organ of interest 112, in the captured sequence of video frames. The sequence of video frames captured in real time or near-real time may be modified such that the generated supplemental information is included in a specific portion in the modified sequence of video frames.

At 428, at least a portion of the internal organ of interest 112 within the body of the human subject 110 may be localized in the surgery based on the generated supplemental information. A portion occupied by the internal organ of interest 112 of the human subject 110 may be localized within the test video frame, based on a convolution of the computed appearance likelihood (i.e., the appearance data) and the estimated plurality of kernel values. At 430, the localized portion within the test video frame may be compared with a localized portion in different test video frames that are a part of the captured sequence of video frames received as a continuous video feed from the image capture device 104.

At 432, a set of markers may be assigned at a contour of the localized portion of the internal organ of interest 112, in the test video frame and different test video frames that are a part of the captured sequence of video frames received as a continuous video feed from the image capture device 104. The supplemental information may further include the assigned set of markers at the contour of the localized portion of the internal organ of interest 112. At 434, display of the generated supplemental information may be controlled on the display device 116 such that the generated supplemental information is continuously overlaid on a specific portion in the modified sequence of video frames as a continuous feed captured by the image capture device, in real time or near-real time. The specific portion may be the contour of the localized portion of the internal organ of interest 112.

At 436, an instruction may be generated to enable navigation of the image capture device 104 or a surgical instrument within the body of the human subject 110 to reach to the localized portion of the internal organ of interest 112 in the surgery. Control passes to end 438.

In accordance with an embodiment of the disclosure, the apparatus for internal organ localization of a subject for providing assistance during surgery may comprise the apparatus 102 (FIG. 1). The apparatus 102 may comprise one or more circuits, such as the circuitry 202 (FIG. 2). The circuitry 202 may be configured to generate test data from a test video frame selected from the captured sequence of video frames. The test data may comprise a plurality of patches of the test video frame. The circuitry 202 may be further configured to compute appearance data of the internal organ of interest 112 in the test video frame, based on the generated test data from the test video frame and specified training data for the internal organ of interest 112. The circuitry 202 may be further configured to determine orientation data of the internal organ of interest 112 within the body of the human subject 110, based on a known orientation of the image capture device and a maximum correlation of the test video frame with a specified anatomical template for the internal organ of interest 112. The circuitry 202 may be further configured to generate, based on the computed appearance data of the internal organ of interest 112 and the determined orientation data of the internal organ of interest 112, supplemental information for the internal organ of interest 112 in the captured sequence of video frames. The circuitry 202 may be further configured to localize at least a portion of the internal organ of interest 112 within the body of the human subject 110 in the surgery based on the generated supplemental information.

Various embodiments of the disclosure may provide a non-transitory computer readable medium and/or storage medium, and/or a non-transitory machine readable medium and/or storage medium with a machine code and/or a set of instructions stored thereon and executable by a machine and/or a computer to provide assistance during surgery in the presence of tissue deformation. The set of instructions in the apparatus 102 may cause the machine and/or computer to perform the steps for localization of an internal organ of a subject to provide assistance during surgery. A sequence of video frames of one or more internal organs in a body of a subject may be captured by insertion of an image capture device in a body of the subject. The apparatus further may include circuitry that computes appearance data of an internal organ of interest in a test video frame selected from the captured sequence of video frames. Orientation data of the internal organ of interest may be determined within the body of the subject based on a known orientation of the image capture device and a maximum correlation of the test video frame with a specified anatomical template for the internal organ of interest. Supplemental information may be generated to localize at least a portion of the internal organ of interest of the subject in the surgery.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system that has an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that falls within the scope of the appended claims.

What is claimed is:

1. An apparatus for providing assistance during surgery, comprising:
    an image capture device configured to capture a sequence of video frames of one or more internal organs of a subject based on insertion of the image capture device in a body of the subject; and
    circuitry communicatively coupled to the image capture device, wherein the circuitry is configured to:
        generate test data from a test video frame selected from the captured sequence of video frames, wherein the test data comprises a plurality of patches of the test video frame;
        compute appearance data of an internal organ of interest in the test video frame, based on the generated test data from the test video frame and specified training data for the internal organ of interest;
        determine orientation data of the internal organ of interest within the body of the subject, based on a known orientation of the image capture device and a maximum correlation of the test video frame with a specified anatomical template for the internal organ of interest; and
        generate, based on the computed appearance data of the internal organ of interest and the determined orientation data of the internal organ of interest, supplemental information for the internal organ of interest in the captured sequence of video frames; and
        localize at least a portion of the internal organ of interest within the body of the subject in the surgery based on the generated supplemental information.

2. The apparatus according to claim 1, wherein the internal organ of interest is an abdominal organ.

3. The apparatus according to claim 1, wherein the circuitry is further configured to:
    receive the captured sequence of video frames of the one or more internal organs of the subject; and
    select the test video frame from the received sequence of video frames based on an area occupied by the internal organ of interest in the test video frame, wherein the area occupied by the internal organ of interest in the test video frame is greater than a threshold area.

4. The apparatus according to claim 1, wherein the circuitry is further configured to extract a set of training patches from the specified training data by a random sampling technique based on the selected test video frame, wherein the circuitry is further configured to utilize the selected set of training patches for estimation of the appearance data.

5. The apparatus according to claim 4, wherein the random sampling technique is a Monte Carlo sampling.

6. The apparatus according to claim 4, wherein the circuitry is further configured to compute a color likelihood of a portion of the test video frame that includes the internal organ of interest based on a comparison of a color component of the portion of the test video frame with a color component in the extracted set of training patches of the specified training data.

7. The apparatus according to claim 6, wherein the circuitry is further configured to compute a texture likelihood of the portion of the test video frame that includes the internal organ of interest based on a comparison of a texture component of the portion of the test video frame with a texture component in the extracted set of training patches of the specified training data.

8. The apparatus according to claim 7, wherein the circuitry is further configured to utilize the color likelihood and the texture likelihood that are computed independent of each other to derive an appearance likelihood of the internal organ of interest in the test video frame, wherein the appearance likelihood corresponds to the estimated appearance data.

9. The apparatus according to claim 1, wherein the circuitry is further configured to compute a plurality of kernel values for the known orientation of the internal organ of interest to estimate the orientation data of the internal organ of interest within the body of the subject.

10. The apparatus according to claim 9, wherein the circuitry is further configured to estimate the plurality of kernel values for a portion of the test video frame that includes the internal organ of interest, based on a similarity of pose information in the specified anatomical template with the test video frame.

11. The apparatus according to claim 10, wherein the circuitry is further configured to localize a portion occupied by the internal organ of interest of the subject within the test video frame, based on a convolution of the appearance data and the estimated plurality of kernel values.

12. The apparatus according to claim 1, wherein the circuitry is further configured to compare the at least the localized portion within the test video frame with a localized portion in different test video frames that are a part of the captured sequence of video frames received as a continuous video feed from the image capture device.

13. The apparatus according to claim 12, wherein the circuitry is further configured to assign a set of markers at a contour of the localized portion of the internal organ of interest, in the test video frame and different test video frames that are the part of the captured sequence of video frames received as the continuous video feed from the image capture device, wherein the supplemental information includes at least the assigned set of markers at the contour of the localized portion of the internal organ of interest.

14. The apparatus according to claim 13, wherein the circuitry is further configured to modify the captured sequence of video frames in real time or near-real time to include the generated supplemental information in a specific portion in the captured sequence of video frames, based on the computed appearance data of the internal organ of interest and the determined orientation data of the internal organ of interest.

15. The apparatus according to claim 14, wherein the circuitry is further configured to control display, at a display device, of the generated supplemental information in the specific portion in the modified sequence of video frames as a continuous feed captured by the image capture device, in real time or near-real time.

16. The apparatus according to claim 1, wherein the specified anatomical template of the internal organ of interest comprises a reference 3D graphic model of the internal organ of interest rendered at a first orientation.

17. The apparatus according to claim 16, wherein the circuitry is further configured to change an orientation of a rendering of the reference 3D graphic model of the internal organ of interest from the first orientation to a second orientation in accordance to an orientation of the internal organ of interest visible in the test video frame.

18. The apparatus according to claim 1, wherein the circuitry is further configured to generate an instruction to enable navigation of the image capture device or a surgical instrument within the body of the subject to reach to the at least the localized portion of the internal organ of interest.

19. A method, comprising:
in an apparatus that comprises circuitry communicatively coupled to an image capture device:
capturing, by the image capture device, a sequence of video frames of one or more internal organs of a subject based on insertion of the image capture device in a body of the subject;
generating, by the circuitry, test data from a test video frame selected from the captured sequence of video frames, wherein the test data comprises a plurality of patches of the test video frame;
computing, by the circuitry, appearance data of an internal organ of interest in the test video frame, based on the generated test data from the test video frame and specified training data for the internal organ of interest;
determining, by the circuitry, orientation data of the internal organ of interest within the body of the subject, based on a known orientation of the image capture device and a maximum correlation of the test video frame with a specified anatomical template for the internal organ of interest; and
generating, by the circuitry, based on the computed appearance data of the internal organ of interest and the determined orientation data of the internal organ of interest, supplemental information for the internal organ of interest in the captured sequence of video frames; and
localizing, by the circuitry, at least a portion of the internal organ of interest within the body of the subject during surgery, based on the generated supplemental information.

20. The method according to claim 19, further comprising receiving, by the circuitry, the captured sequence of video frames of the one or more internal organs of the subject, wherein the test video frame is selected from the captured sequence of video frames based on an area occupied by the internal organ of interest in the test video frame, wherein the area occupied by the internal organ of interest in the test video frame is greater than a threshold area.

* * * * *